(12) United States Patent
Toellner (10) Patent No.: US 10,874,781 B2
(45) Date of Patent: Dec. 29, 2020

(54) SYSTEM FOR INTRODUCING A PUMP

(71) Applicant: ECP ENTWICKLUNGSGESELLSCHAFT MBH, Berlin (DE)

(72) Inventor: Thomas Toellner, Berlin (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 0 days.

(21) Appl. No.: 14/985,217

(22) Filed: Dec. 30, 2015

(65) Prior Publication Data

US 2016/0106895 A1 Apr. 21, 2016

Related U.S. Application Data

(63) Continuation of application No. 13/261,529, filed as application No. PCT/EP2011/003187 on Jun. 24, 2011, now Pat. No. 9,974,893.

(Continued)

(30) Foreign Application Priority Data

Jun. 25, 2010 (EP) .................... 10075277

(51) Int. Cl.
*A61M 1/10* (2006.01)
*A61M 1/12* (2006.01)
(Continued)

(52) U.S. Cl.
CPC ............ *A61M 1/1012* (2014.02); *A61M 1/10* (2013.01); *A61M 1/101* (2013.01);
(Continued)

(58) Field of Classification Search
CPC .... A61M 1/10; A61M 1/1024; A61M 1/1034; A61M 1/125; A61M 1/101; A61M 25/01; A61M 25/0668
(Continued)

(56) References Cited

U.S. PATENT DOCUMENTS

| 2,350,534 A | 6/1944 | Rosinger |
| 2,649,052 A | 8/1953 | Weyer |

(Continued)

FOREIGN PATENT DOCUMENTS

| CA | 1008330 A | 4/1977 |
| CA | 2311977 A1 | 12/2000 |

(Continued)

OTHER PUBLICATIONS

Brochure Impella Pump system of Impella CardioSystems AG, "Turning Lives Around," Aug. 2003 (4 pages).
(Continued)

*Primary Examiner* — Carl H Layno
*Assistant Examiner* — Erin M Piateski
(74) *Attorney, Agent, or Firm* — White & Case LLP (57) ABSTRACT

The invention resides in the field of introducing fluid pumps into a lumen and relates to a system for introducing a pump into a lumen which comprises a first sheath and a pump to be introduced into the first sheath, or a system which has a pump with a distal pump unit and a shaft catheter which emerges proximally to the pump unit. According to the invention one or two sheaths are used, the distal pump unit being pulled firstly into the distal end of one sheath, in order to avoid damage to a shaft catheter. Subsequently, the sheath receiving the pump unit is transferred into a further sheath or a receiving lumen.

21 Claims, 7 Drawing Sheets

Related U.S. Application Data (60) Provisional application No. 61/358,496, filed on Jun. 25, 2010.

(51) Int. Cl.
*A61M 25/01* (2006.01)
*A61M 25/06* (2006.01)

(52) U.S. Cl.
CPC ........ *A61M 1/1024* (2014.02); *A61M 1/1034* (2014.02); *A61M 1/122* (2014.02); *A61M 1/125* (2014.02); *A61M 25/01* (2013.01); *A61M 25/0668* (2013.01); *A61M 1/1008* (2014.02)

(58) Field of Classification Search
USPC .......................................................... 600/16
See application file for complete search history.

(56) References Cited

U.S. PATENT DOCUMENTS

| | | |
|---|---|---|
| 3,333,127 A | 7/1967 | Congdon et al. |
| 3,354,833 A | 11/1967 | Laing |
| 3,489,145 A | 1/1970 | Judson et al. |
| 3,510,229 A | 5/1970 | Smith et al. |
| 3,568,659 A | 3/1971 | Karnegis |
| 3,802,551 A | 4/1974 | Somers |
| 3,812,812 A | 5/1974 | Hurwitz |
| 3,936,683 A | 2/1976 | Walker |
| 4,014,317 A | 3/1977 | Bruno |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,207,028 A | 6/1980 | Ridder |
| 4,420,851 A | 12/1983 | Wiener |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier et al. |
| 4,801,243 A | 1/1989 | Norton |
| 4,817,613 A | 4/1989 | Jaraczewski et al. |
| 4,846,152 A | 7/1989 | Wampler et al. |
| 4,895,557 A | 1/1990 | Moise et al. |
| 4,919,647 A | 4/1990 | Nash |
| 4,957,504 A | 9/1990 | Chardack |
| 4,969,865 A | 11/1990 | Hwang et al. |
| 4,984,972 A | 1/1991 | Clausen et al. |
| 4,995,857 A | 2/1991 | Arnold |
| 5,011,469 A | 4/1991 | Buckberg et al. |
| 5,017,103 A | 5/1991 | Dahl |
| 5,037,403 A | 8/1991 | Garcia |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,147,186 A | 9/1992 | Buckholtz |
| 5,158,279 A | 10/1992 | Laffey et al. |
| 5,163,431 A | 11/1992 | Griep |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,250,059 A | 10/1993 | Andreas et al. |
| 5,275,580 A | 1/1994 | Yamazaki |
| 5,357,963 A | 10/1994 | Mayol et al. |
| 5,373,619 A | 12/1994 | Fleischhacker et al. |
| 5,376,114 A | 12/1994 | Jarvik |
| 5,405,383 A | 4/1995 | Barr |
| 5,421,338 A | 6/1995 | Crowley et al. |
| 5,480,392 A | 1/1996 | Mous |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,827,171 A | 10/1998 | Dobak, III et al. |
| 5,851,174 A | 12/1998 | Jarvik et al. |
| 5,863,179 A | 1/1999 | Westphal et al. |
| 5,882,329 A | 3/1999 | Patterson et al. |
| 5,888,241 A | 3/1999 | Jarvik |
| 5,938,672 A | 8/1999 | Nash |
| 5,954,745 A | 9/1999 | Gertler et al. |
| 5,984,944 A * | 11/1999 | Forber ............ A61B 17/12022 606/191 |
| 6,001,078 A | 12/1999 | Reekers |
| 6,030,397 A | 2/2000 | Monetti et al. |
| 6,054,788 A | 4/2000 | Dombrovski et al. |
| 6,083,260 A | 7/2000 | Aboul-Hosn |
| 6,123,725 A | 9/2000 | Aboul-Hosn |
| 6,129,704 A | 10/2000 | Forman et al. |
| 6,152,693 A | 11/2000 | Olsen et al. |
| 6,168,624 B1 | 1/2001 | Sudai |
| 6,183,220 B1 | 2/2001 | Ohara et al. |
| 6,210,318 B1 * | 4/2001 | Lederman ........... A61M 1/1072 600/18 |
| 6,245,007 B1 | 6/2001 | Bedingham et al. |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,350,278 B1 * | 2/2002 | Lenker ...................... A61F 2/07 623/1.12 |
| 6,387,125 B1 | 5/2002 | Yamazaki et al. |
| 6,413,222 B1 | 7/2002 | Pantages et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,517,528 B1 | 2/2003 | Pantages et al. |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,247 B2 | 3/2003 | Shannon |
| 6,537,315 B2 | 3/2003 | Yamazaki et al. |
| 6,544,216 B1 | 4/2003 | Sammler et al. |
| 6,592,612 B1 | 7/2003 | Samson et al. |
| 6,652,548 B2 | 11/2003 | Evans et al. |
| 6,656,153 B1 | 12/2003 | Sakai et al. |
| 6,719,791 B1 | 4/2004 | Nusser et al. |
| 6,841,910 B2 | 1/2005 | Gery |
| 6,858,001 B1 | 2/2005 | Aboul-Hosn |
| 6,860,713 B2 | 3/2005 | Hoover |
| 6,945,977 B2 | 9/2005 | Demarais et al. |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,646,376 B2 | 1/2010 | Blersch |
| 7,731,675 B2 | 6/2010 | Aboul-Hosn et al. |

(56) References Cited

U.S. PATENT DOCUMENTS

| | | | |
|---|---|---|---|
| 7,841,976 B2 | 11/2010 | McBride et al. | |
| 7,927,068 B2 | 4/2011 | McBride et al. | |
| 7,934,909 B2 | 5/2011 | Nuesser et al. | |
| 8,439,859 B2 | 5/2013 | Pfeffer et al. | |
| 8,888,728 B2 | 11/2014 | Aboul-Hosn et al. | |
| 2001/0000528 A1 | 4/2001 | Cho | |
| 2002/0087119 A1* | 7/2002 | Parodi | A61B 17/12022 604/103.07 |
| 2002/0123661 A1 | 9/2002 | Verkerke et al. | |
| 2002/0151799 A1 | 10/2002 | Pantages et al. | |
| 2002/0183777 A1* | 12/2002 | Shannon | A61M 25/104 606/192 |
| 2003/0135940 A1 | 7/2003 | Lev et al. | |
| 2003/0208097 A1 | 11/2003 | Aboul-Hosn et al. | |
| 2003/0231959 A1 | 12/2003 | Snider | |
| 2003/0233143 A1 | 12/2003 | Gharib et al. | |
| 2004/0022640 A1 | 2/2004 | Siess et al. | |
| 2004/0044266 A1* | 3/2004 | Siess | A61M 1/101 600/16 |
| 2004/0046466 A1 | 3/2004 | Siess et al. | |
| 2004/0093074 A1 | 5/2004 | Hildebrand et al. | |
| 2004/0113502 A1 | 6/2004 | Li et al. | |
| 2004/0147877 A1 | 7/2004 | Heuser | |
| 2004/0193046 A1 | 9/2004 | Nash et al. | |
| 2004/0215222 A1 | 10/2004 | Krivoruchko | |
| 2004/0215228 A1 | 10/2004 | Simpson et al. | |
| 2004/0260237 A1 | 12/2004 | Squadrito | |
| 2005/0135942 A1 | 6/2005 | Wood et al. | |
| 2006/0008349 A1 | 1/2006 | Khaw | |
| 2006/0062672 A1* | 3/2006 | McBride | A61M 1/101 416/142 |
| 2006/0195004 A1 | 8/2006 | Jarvik | |
| 2007/0118072 A1 | 5/2007 | Nash | |
| 2008/0004569 A1 | 1/2008 | McCrystle et al. | |
| 2008/0004571 A1 | 1/2008 | Voss | |
| 2008/0097386 A1 | 4/2008 | Osypka | |
| 2008/0103591 A1 | 5/2008 | Siess | |
| 2008/0132747 A1 | 6/2008 | Shifflette | |
| 2008/0183136 A1 | 7/2008 | Lenker et al. | |
| 2008/0262584 A1 | 10/2008 | Bottomley et al. | |
| 2008/0306327 A1 | 12/2008 | Shifflette | |
| 2009/0062597 A1 | 3/2009 | Shifflette | |
| 2009/0088609 A1 | 4/2009 | Schmitz-Rode et al. | |
| 2009/0093764 A1 | 4/2009 | Pfeffer et al. | |
| 2009/0093796 A1 | 4/2009 | Pfeffer et al. | |
| 2009/0218728 A1 | 9/2009 | Moyer | |
| 2009/0227892 A1 | 9/2009 | Krombach et al. | |
| 2010/0004730 A1 | 1/2010 | Benjamin et al. | |
| 2010/0041939 A1 | 2/2010 | Siess | |
| 2010/0210895 A1 | 8/2010 | Aboul-Hosn et al. | |
| 2010/0268017 A1 | 10/2010 | Siess | |
| 2011/0004046 A1 | 1/2011 | Campbell et al. | |
| 2011/0071338 A1 | 3/2011 | McBride et al. | |
| 2011/0238172 A1 | 9/2011 | Akdis | |
| 2011/0275884 A1 | 11/2011 | Scheckel | |
| 2012/0039711 A1 | 2/2012 | Roehn | |
| 2012/0041254 A1 | 2/2012 | Scheckel | |
| 2012/0046648 A1 | 2/2012 | Scheckel | |
| 2012/0093628 A1 | 4/2012 | Liebing | |
| 2012/0101455 A1 | 4/2012 | Liebing | |
| 2012/0142994 A1 | 6/2012 | Toellner | |
| 2012/0184803 A1 | 7/2012 | Simon et al. | |
| 2012/0224970 A1 | 9/2012 | Schumacher et al. | |
| 2012/0234411 A1 | 9/2012 | Scheckel | |
| 2012/0237353 A1 | 9/2012 | Schumacher et al. | |
| 2012/0237357 A1 | 9/2012 | Schumacher et al. | |
| 2012/0264523 A1 | 10/2012 | Liebing | |
| 2012/0265002 A1 | 10/2012 | Roehn et al. | |
| 2012/0294727 A1 | 11/2012 | Roehn | |
| 2012/0301318 A1 | 11/2012 | Er | |
| 2012/0308406 A1 | 12/2012 | Schumacher | |
| 2013/0019968 A1 | 1/2013 | Liebing | |
| 2013/0041202 A1 | 2/2013 | Toellner | |
| 2013/0060077 A1 | 3/2013 | Liebing | |
| 2013/0066139 A1 | 3/2013 | Wiessler et al. | |
| 2013/0066140 A1 | 3/2013 | McBride et al. | |
| 2013/0085318 A1 | 4/2013 | Toellner | |
| 2013/0177409 A1 | 7/2013 | Schumacher et al. | |
| 2013/0177432 A1 | 7/2013 | Toellner et al. | |
| 2013/0204362 A1 | 8/2013 | Toellner et al. | |
| 2013/0237744 A1 | 9/2013 | Pfeffer et al. | |
| 2014/0039465 A1 | 2/2014 | Schulz et al. | |
| 2015/0073202 A1 | 3/2015 | Aboul-Hosn et al. | |

FOREIGN PATENT DOCUMENTS

| | | |
|---|---|---|
| CA | 2613175 A1 | 1/2007 |
| CA | 2632420 A1 | 6/2007 |
| CA | 2701809 A1 | 4/2009 |
| CA | 2701810 A1 | 4/2009 |
| CN | 1355715 A | 6/2002 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 4414903 A1 | 11/1995 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 100 59 714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102005039950 A1 | 3/2007 |
| DE | 102010011998 A1 | 9/2010 |
| EP | 0364293 | 4/1990 |
| EP | 0445782 | 9/1991 |
| EP | 0480102 A1 | 4/1992 |
| EP | 0560000 A2 | 9/1993 |
| EP | 0629412 A2 | 12/1994 |
| EP | 0768091 A1 | 4/1997 |
| EP | 0768900 A1 | 4/1997 |
| EP | 0884064 A2 | 12/1998 |
| EP | 0914171 A2 | 5/1999 |
| EP | 0916359 A1 | 5/1999 |
| EP | 951302 A2 | 10/1999 |
| EP | 1019117 A1 | 7/2000 |
| EP | 1034808 A1 | 9/2000 |
| EP | 1066851 A1 | 1/2001 |
| EP | 1114648 A2 | 7/2001 |
| EP | 1207934 A2 | 5/2002 |
| EP | 1337288 A1 | 8/2003 |
| EP | 1651290 A1 | 5/2006 |
| EP | 2047872 A | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| FR | 2788223 A1 | 7/2000 |
| GB | 2239675 A | 7/1991 |
| JP | H-04126158 | 4/1992 |
| RU | 2229899 C2 | 6/2004 |
| WO | WO-9202263 A1 | 2/1992 |
| WO | WO-9302732 A1 | 2/1993 |
| WO | WO-9303786 A1 | 3/1993 |
| WO | WO-9314805 A1 | 8/1993 |
| WO | WO-9401148 A1 | 1/1994 |
| WO | WO-9405347 A1 | 3/1994 |
| WO | WO-9409835 A1 | 5/1994 |
| WO | WO-9420165 A2 | 9/1994 |
| WO | WO-9523000 A2 | 8/1995 |

(56) References Cited

FOREIGN PATENT DOCUMENTS

| | | |
|---|---|---|
| WO | WO-9618358 A1 | 6/1996 |
| WO | WO-9625969 A2 | 8/1996 |
| WO | WO-9744071 A1 | 11/1997 |
| WO | WO-9853864 A1 | 12/1998 |
| WO | WO-9919017 A1 | 4/1999 |
| WO | WO-9944651 A1 | 9/1999 |
| WO | WO-99/58170 A1 | 11/1999 |
| WO | WO-2000019097 | 4/2000 |
| WO | WO-0027446 A1 | 5/2000 |
| WO | WO-0043054 A2 | 7/2000 |
| WO | WO-2000043053 | 7/2000 |
| WO | WO-0062842 A1 | 10/2000 |
| WO | WO-2001007760 | 2/2001 |
| WO | WO-2001007787 | 2/2001 |
| WO | WO-2001083016 | 11/2001 |
| WO | WO-2002022200 | 3/2002 |
| WO | WO-02/43791 A1 | 6/2002 |
| WO | WO-2003057013 | 7/2003 |
| WO | WO-2003103745 | 12/2003 |
| WO | WO-2005002646 A1 | 1/2005 |
| WO | WO-2005016416 A1 | 2/2005 |
| WO | WO-2005021078 A1 | 3/2005 |
| WO | WO-2005030316 A1 | 4/2005 |
| WO | WO-2005032620 A1 | 4/2005 |
| WO | WO-2005081681 A2 | 9/2005 |
| WO | WO-2006020942 A1 | 2/2006 |
| WO | WO-2006034158 A2 | 3/2006 |
| WO | WO-2006133209 A1 | 12/2006 |
| WO | WO-2007003351 A1 | 1/2007 |
| WO | WO-2007103390 A2 | 9/2007 |
| WO | WO-2007103464 A2 | 9/2007 |
| WO | WO-2007112033 A2 | 10/2007 |
| WO | WO-2008017289 A2 | 2/2008 |
| WO | WO-2008034068 A2 | 3/2008 |
| WO | WO-2008054699 A2 | 5/2008 |
| WO | WO-2008106103 A2 | 9/2008 |
| WO | WO-2008116765 A2 | 10/2008 |
| WO | WO-2008124696 A1 | 10/2008 |
| WO | WO-2008137352 A1 | 11/2008 |
| WO | WO-2008137353 A1 | 11/2008 |
| WO | WO-2009015784 A1 | 2/2009 |
| WO | WO-2010063494 A1 | 6/2010 |
| WO | WO-2010133567 A1 | 11/2010 |
| WO | WO-2013034547 A1 | 3/2013 |
| WO | WO-2013092971 A1 | 6/2013 |
| WO | WO-2013093001 A2 | 6/2013 |
| WO | WO-2013093058 A1 | 6/2013 |

OTHER PUBLICATIONS

Buecker A et al., "Use of a Nonmetallic Guide Wire for Magnetic Resonance-Guided Coronary Artery Catheterization," Investigative Radiology, 39:11, pp. 656-660 (2004).
Compendium of Technical and Scientific Information for the Hemopump Temporary Cardiac Assist System, 1988 (15 pages).
Dekker, Andre, et al, "Efficacy of a New Intraaortic Propeller Pump vs the Intraaortic Balloon Pump," Chest Journal; Jun. 2003 (7 pages).
Frazier, O.H., et al, "First Human Use of the Hemopump, A Cather-Mounted Ventricular Assist Device," Ann Thorac Surg., Feb. 1990; 49(2): pp. 299-304.
International Preliminary Report on Patentability, from PCT/EP09/008858, dated Jun. 7, 2011.
JOMED Reitan Catheter Pump Brochure, www.jomed.com/rcp (undated) (6 pages).
Lueger, Lexikon der Technik, "Lexikon der Feinwerktechnik", vol. 13, Deutsche Verlags-Anstalt GmbH, Stuttgart, seite 551 (4 pages) (1968).
Reitan, Oyvind et al, "Hydrodynamic Properties of a New Percutaneous Intra-aortic Axial Flow Pump," ASAIO Journal; May-Jun.; vol. 16; 6 pages (2000).
Rothman, Martin T, "The Reitan Catheter Pump: A New Versatile Approach for Hemodynamic Support," London Chest Hospital Barts & The Long NHS Trust, presented at TCT Conference, Oct. 24-26, 2006, (40 pages).
Schmitz-Rode, T et al, "An Expandable Percutaneous Catheter Pump for Left Ventricular Support," Journal of the American College of Cardiology, 45:11, pp. 1856-1861 (2005).
Schmitz-Rode, T et al, "Temporary Pulmonary Stent Placement as Emergency Treatment of Pulmonary Embolism," Journal of the American College of Cardiology, 48:4, pp. 812-816 (2006).
Siess, Thorsten, "Systemanalyseund Entwicklung intravasaler Rotationspumpen zur Herzunterstutzung," Helmholtz-Institut, Jun. 24, 1998 (105 pages) and partial English translation (39 pages).
Verma, al, "Evaluation of a Newly Developed Percutaneous Thrombectomy Basket Device in Sheep with Central Pulmonary Embolisms," Investigative Radiology, 41:10, pp. 729-734 (2006).
Wampler, Richard, K., "In Vivo Evaluation of a Peripheral Vascular Access Axial Flow Blood Pump," ASAIO Trans., Jul.-Sep. 1988;34(3): pp. 450-454.

* cited by examiner

SYSTEM FOR INTRODUCING A PUMP

This application is a continuation of U.S. patent application Ser. No. 13/261,529, filed Nov. 27, 2012, now U.S. Pat. No. 9,974,893, issued May 22, 2018, which is a national stage entry of PCT Application PCT/EP2011/003 187, filed Jun. 24, 2011 (currently published), which claims priority to U.S. Patent Application No. 61/358,496, filed on Jun. 25, 2010 (currently expired), and European Patent Application No. 10075277.3, filed Jun. 25, 2010, the contents of all of which are incorporated by reference herein in their entirety. International Application No. PCT/EP2011/003187 was published under PCT Article 21(2) in English.

BACKGROUND OF THE INVENTION

The invention resides in the field of introducing fluid pumps into a lumen and relates to a system for introducing a pump into a lumen, which comprises a first sheath and a pump to be introduced into the first sheath, or a system which has a pump with a distal pump unit and a shaft catheter which emerges proximally to the pump unit.

The application can hence be provided, on the one hand, in the minimally invasive medical field, for example as a blood pump for heart assistance, and, on the other hand, also use in agitators or as a drive element is conceivable.

BRIEF SUMMARY OF THE INVENTION

The invention can display special advantages by the possible miniaturisation in the medical field. Techniques for introducing fluid pumps, in particular into natural body lumina, are known in detail in prior art. Thus reference is made inter alia to the Seldinger technique for introducing an introducer sheath into a vascular system. The technique and possible variants are intended to be explained in more detail with reference to FIG. 1.

Figure 1:
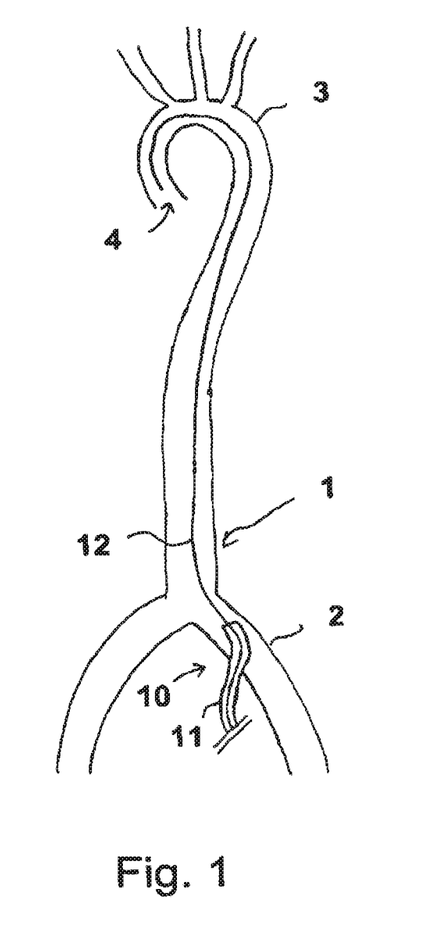
FIG. 1 a schematic overview of a vascular system with an introduced first sheath.

A schematic human vascular system 1 is shown in FIG. 1. In the groin region there is one of the femoral arteries 2 which is connected to the aortic arch via a main artery and subsequently opens into the ventricle 4. With the help for example of the Seldinger technique, firstly an introducer sheath 10 is introduced into the femoral artery 2. Firstly, the femoral artery or any blood vessel is hereby punctured with a steel cannula with a cutting tip. A guide wire 12 is pushed through the steel cannula introduced into the puncture and is introduced retrogressively via the aortic arch 3 into the left ventricle 4. After removing the puncturing cannula, the first sheath 10 which is configured as introducer sheath and comprises a tubular portion 11 is threaded onto the guide wire and introduced into the vascular system through the punctured point, the sheath being introduced into the lumen of the vascular system merely by a small distance. Subsequently, a fluid pump is introduced into the vascular system through the introducer sheath 10.

Such a method is known for example from WO 02/43791 A1. After the introducer sheath, as represented in FIG. 1, has been introduced into the vascular system, a heart pump is pushed forwards along the guide wire 12 into the left ventricle 4. The pump, in particular a distal pump unit, is thereby pushed outside the sheath through the vascular system towards the ventricle.

Modern fluid pumps often rotate at high speeds in order to be able to convey a corresponding quantity of fluid per minute. Such a blood pump can be deduced for example from the above-mentioned WO 02/43791 A1 or from EP 2 047 872 A1. The latter shows a pump which has a distal pump unit, a shaft catheter abutting against the proximal end of the distal pump unit, the shaft catheter in turn being able to be connected to a drive unit for giving the fluid pump.

One disadvantage in the previously known systems for introducing a pump into a lumen is the great danger of damaging the shaft extending in the shaft catheter, which has a negative effect on the lifespan or the useful life of the pump unit.

Starting from the known state of the art, it is the object of the present invention to reduce the danger of damaging the shaft catheter of a pump.

The object is achieved by a system according to the features of claim 1 or with the help of a system according to the features of claim 12. Furthermore, methods for introducing and removing pumps are included by the invention.

Further embodiments are cited in the subordinate and coordinated claims.

A first aspect of the invention is offered by a system for introducing a (preferably expandable) pump (for particular preference self-expandable rotary pump) into a lumen, the system comprising a first sheath and a pump to be introduced into the first sheath and the first sheath having a first sheath lumen which extends from a distal end to a proximal end for introducing the pump.

A self-expanding pump can be decompressed on the basis of being taken out of the sheath since the sheath no longer restricts the radius of the pump. Alternatively, the self-expanding pump can have a material which changes its state on the basis of the flow conditions, the temperature prevailing in the vascular system or the pressure and thus effects decompression of the pump unit taken out of the sheath.

With regard to the details of the pump (according to the aspects of the invention presented in this application), reference is made to the entire disclosures of U.S. Provisional Application No. 61/120,095, filed on Dec. 5, 2008, No. 61/149,753, filed on Feb. 4, 2009 No. 61/151,964, filed on Feb. 12, 2009, No. 61/161,125, filed on Mar. 18, 2009 No. 61/162,710, filed on Mar. 24, 2009, No. 61/173,666, filed on Apr. 29, 2009, No. 61/175,519, filed on May 5, 2009, No. 61/220,292, filed on Jun. 25, 2009, No. 61/231,787, filed on Aug. 6, 2009, No. 61/244,592, filed on Sep. 22, 2009, No. 61/244,600, filed on Sep. 22, 2009, No. 61/244,608, filed on Sep. 22, 2009, No. 61/244,614, filed on Sep. 22, 2009, No. 61/254,315, filed on Oct. 23, 2009, No. 61/254,339, filed on Oct. 23, 2009, No. 61/289,569, filed on Dec. 23, 2009, No. 61/289,645, filed on Dec. 23, 2009, No. 61/289,656, filed on Dec. 23, 2009, No. 61/293,270, filed on Jan. 8, 2010, No. 61/297,858, filed on Jan. 25, 2010, No. 61/298,581, filed on Jan. 27, 2010, No. 61/310,750, filed on Mar. 5, 2010, No. 61/345,253, filed on May 17, 2010, No. 61/358,496, filed on Jun. 25, 2010, No. 61/364,559, filed on Jul. 15, 2010, No. 61/364,578, filed on Jul. 15, 2010, No. 61/364,595, filed on Jul. 15, 2010, and No. 61/451,222, filed on Mar. 10, 2011, which are hereby incorporated by reference in this application in their entirety.

There is understood by the term sheath in the present application, essentially a lumen which is surrounded by a casing and has a distal and a proximal opening. Preferably, the sheath is configured such that this can receive a shaft catheter, for example a shaft catheter with a diameter of 5-15 Fr, preferably 7-11 Fr. In addition, a sheath is preferably flexible so that this can be guided through a natural body lumen. This applies both to the first and the second sheath.

According to the invention, the system comprises furthermore a second sheath with a second sheath lumen which extends from a distal end to a proximal end and in which the pump is retained in a guidable manner. The second sheath is thereby configured such that it can be coupled to the first sheath for transferring the pump from the second into the first sheath.

The second sheath offers additional protection for the shaft catheter during introduction of the pump. In this way, an improved introduction of the pump into the first sheath or into the first sheath lumen is made possible.

In the sense of the present invention, "sheath" implies an object through which something different can be guided. Such a sheath can, but need not necessarily, have a haemostatic valve.

Since threading the pump into a sheath is associated generally with great care and hence associated with considerable time expenditure, the second sheath makes threading the pump unit into the same possible before the actual transfer of the pump into the lumen which receives the pump. In other words, the pump can be inspected firstly well before an operation and subsequently threaded into the second sheath, preferably pulled in, threading in being able to be undertaken without pressure of time.

At the time of the operation, the second sheath in which the pump is firstly retained must now be coupled merely to the first sheath, and the pump can be transferred directly from the second into the first sheath. This reduces the probability of damaging the pump or the shaft and enables thus an improved running performance or running time of the pump itself. Also, the time expenditure for introducing the pump which is required during for example an operation is reduced.

A second aspect of the invention relates to a system which can be used in the above-mentioned system, having a pump which comprises a distal pump unit and a shaft catheter which emerges proximally to the pump unit. In addition to the pump, the system has furthermore a sheath with a sheath rumen which is disposed proximally to the distal pump unit, the sheath lumen surrounding a portion of the shaft catheter. The feature termed merely sheath is designated in the system of the first aspect of the invention generally as second sheath. Such features relate to the system according to the second aspect.

The sheath is configured such that the sheath can be displaced along the shaft catheter in the direction of the distal pump unit and the distal pump unit can be introduced into the sheath lumen. This presupposes that the inner diameter of the sheath lumen is greater than the outer diameter of the shaft catheter.

In the system consisting of the pump and the sheath, it is advantageous in particular that pulling can take place on the shaft catheter for puffing in the distal pump unit into the distal end of the sheath. Since, when pulling the shaft, the danger of distortions or damage or bending of the shaft relative to pressing in or pushing in the device into a sheath is significantly reduced, the running time or lifespan of the pump unit is improved relative to the conventional methods for introducing the pump and the systems used there.

After the pump has been pulled into the sheath and the distal end of the distal pump unit is situated partially or completely proximally to the distal end of the sheath, the system of the second aspect can be coupled, according to the first aspect of the invention, to a first sheath so that more simple introduction of the pump unit into the lumen which ultimately receives the pump, such as e.g. a blood vessel, is achieved.

According to a third aspect of the invention, the systems of the first or second aspect of the invention can be further improved. The third aspect comprises a device for retaining a portion of the sheath of the second aspect or of the second sheath of the first aspect. The device for retaining the portion of the sheath is thereby configured such that it can retain the sheath frictionally, on the one hand, and on the other hand, prevent deformation, in particular bending, of the sheath in the retained region. Due to the device for retaining a portion of the sheath, a possibly present intrinsic reinforcement of the sheath, for example in the form of a wire mesh, is not required since the retaining device effects reinforcement of a portion of the sheath. This leads to the fact the bending of the shaft when pulling the pump into the lumen of the sheath is not possible and when transferring the pump from the sheath retained by the device into the first sheath is possible but made difficult.

The three aspects described in the preceding paragraphs each form per se an independent patentable part of the invention. Although the third aspect, i.e. the device for retaining a portion of a sheath, has been described merely as an improvement to the system of the second aspect, an independent significance is also attributed to it. The common inventive idea is to introduce the pomp into a second sheath before introduction into the lumen which is to receive the pump without pressure of time.

All three aspects are suitable per se for preventing bending of the shaft of a pump.

Further embodiments of the different aspects are subsequently dealt with.

In one embodiment, of the first aspect of the invention, the first sheath lumen has, in regions, a smaller inner cross-sectional area, preferably a smaller inner diameter, than the second sheath lumen. This has the advantage that threading the pump into the second sheath can be undertaken in a simplified manner. A ratio between 1:1 and 1:1.2 is possible as a suitable size ratio of the inner cross-sectional area of the first sheath lumen to that of the second sheath lumen.

In a further embodiment of the system of the first aspect, the first sheath comprises a first sheath valve at the proximal end thereof. With the help of the sheath valve, the introducer sheath can firstly he introduced into the lumen receiving the pump and leakage of a fluid out of the pump can be prevented.

The sheath valve is thereby preferably configured such that it has a wider inner cross-section than the sheath lumen. Also a conically tapering shape of the sheath valve is included by the embodiment. The sheath valve thereby tapers horn its proximal end to the distal end, i.e. towards that end at which it is connected to the sheath lumen. Alternatively or in combination, the first sheath lumen can be configured such that this widens in the region of connection between the sheath lumen and the sheath valve.

The sheath is configured according to the invention such that the distal end of the second sheath can be introduced at least partially into the first sheath valve and the coupling between the first and second sheath is produced in this way.

In one embodiment of the first and second aspect of the invention, the second sheath is a tear-off sheath or a "peel-away" sheath which can be torn off over its entire length. Sheaths of this type have for example a molecular structure which facilitates tearing off from the proximal end towards the distal end. The tear-off sheath can however also be configured to be able to be torn off for example by a material tapering in the manner of a predetermined breaking point or by a longitudinally inserted tear-off wire or thread. As a result, the second sheath, after the pump has been transferred from the second sheath into the first sheath, can be torn off and withdrawn from the pump, in particular from the shaft catheter extending therein. The second sheath represents, in this variant, a feature of the invention which is connected to the pump merely before introduction into the lumen which receives the pump.

In a further embodiment of the first and second aspect of the invention, the first and the second sheath comprise a plastic material which can be provided, in a further embodiment, with a strengthening or reinforcing structure. Plastic material represents a particularly suitable material choice in the medical field.

In an embodiment of the third aspect, the device for retaining a portion of the second sheath comprises a cavity in which the portion of the second sheath can be retained frictionally. This can be achieved for example via a roughened surface of the cavity. Another possibility resides in configuring the inner cross-sectional area of the cavity minimally less than the outer cross-sectional area of the second sheath. As a result of the fact that the device has a cavity, the surfaces surrounding the cavity can serve as retaining surface for an operator of the system. Also as a result, damage to the shaft is avoided. There is possible as material, for example, metal or even a plastic material in order to avoid the transmission of pathogens from the device to the sheath. In the case of use in a human or animal body, preferably biocompatible materials should be used.

In a further embodiment of the third aspect, the device is configured such that the second sheath can be received, over preferably at least half of its length, by the device for retaining the second sheath.

In a further embodiment, the device is configured such that the retained portion of the second sheath comprises a curvature of less than 10°, preferably less than 5°, particularly preferred less than 1°. Due to a curvature of the second sheath, the danger of the shaft bending increases. This can be avoided by a corresponding configuration of the device for retaining a portion of the second sheath.

By means of a curvature of the receiving region of the second sheath on the device, the second sheath is fixed axially without restricting the lumen L2 of the second sheath. For this purpose, the $2^{nd}$ sheath should have an appropriate bending resistance. Alternatively, the $2^{nd}$ sheath can also have a curvature and the device can be straight (or both curved).

Figures 14, 15A, 15B:
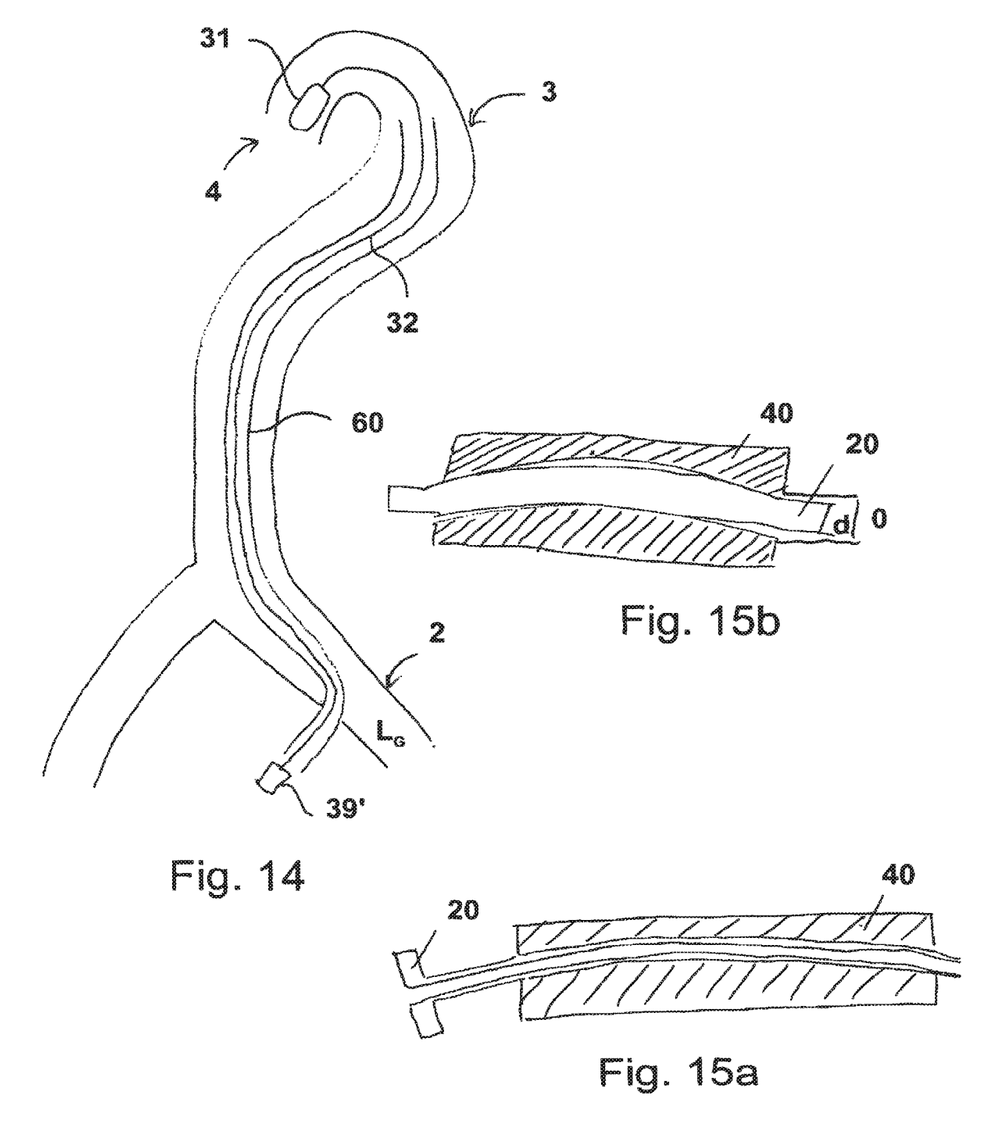
FIG. 14 an embodiment of a long sheath and the arrangement thereof during the operating state of the pump unit.
FIGS. 15a and 15b sketches for clarification of curves.

For this purpose, a system according to the invention provides that the deviations from the straightness of the second sheath in the clamped region and of the device for retaining a portion of the second sheath are together greater than the difference of the inner diameter of the device for retaining a portion of the second sheath and of the outer diameter of the second sheath, see FIGS. 15a and 15b.

The system according to the first aspect can be used in conjunction with a system according to the second aspect such that firstly the first sheath is introduced into the lumen which subsequently receives the pump such that the proximal end of the first sheath is accessible outside the receiving lumen. Before or thereafter, the distal end of the pump can be moved into the sheath lumen of the second sheath, preferably can be pulled into the second sheath with the help of a system according to the second aspect.

For this purpose, the second sheath can be reinforced at least axially in the distal region thereof. Hence bending of the pump or of the second sheath when pulling the pump into the sheath can be prevented.

Subsequently, the distal end of the second sheath is coupled to the proximal end of the first sheath and the pump is transferred from the second sheath into the first sheath.

In one embodiment, the distal end of the pump is subsequently guided through the distal end of the first sheath lumen into the lumen which receives the pump.

In one method for designing the pump, the distal pump unit which is placed distally to the distal end of the sheath remaining in the vascular system is pulled into the sheath and subsequently removed from the receiving lumen through the sheath. Alternatively, the pump can be removed together with the receiving lumen.

In one embodiment of the method for designing the pump, the distal end of the sheath is situated during the operating state of the pump unit less than 20 cm, preferably less than 10 cm, away from the operating location of the pump unit. As a result, transport of the primp unit to the operating location and away from this is simplified. Furthermore, the vascular system is hereby protected from lesions by the pump (during transport of the same).

The present patent application relates in addition to a catheter pump, which can be introduced into human or animal vessels in a compressed state and can be operated in an expanded state in a lumen of the human or animal body in order to convey a fluid, the catheter pump having a rotor far conveying fluid, a housing which surrounds the rotor and is at least partially fluid-permeable and also an introducer sheath close to the rotor, wherein, during transfer from the expanded state into the compressed state, the housing can be introduced into the introducer sheath for narrowing of the diameter at least in regions, and this narrowing of the diameter of the housing is dimensioned such that also the diameter (i.e. the largest outer diameter) of the rotor is reduced by the narrowing of the diameter of the housing from the expanded state to the compressed state.

The invention described in the preceding paragraph is per se for catheter pumps an independent invention so that the applicant reserves the right to direct a separate partial application thereto subsequently.

Figure 4:
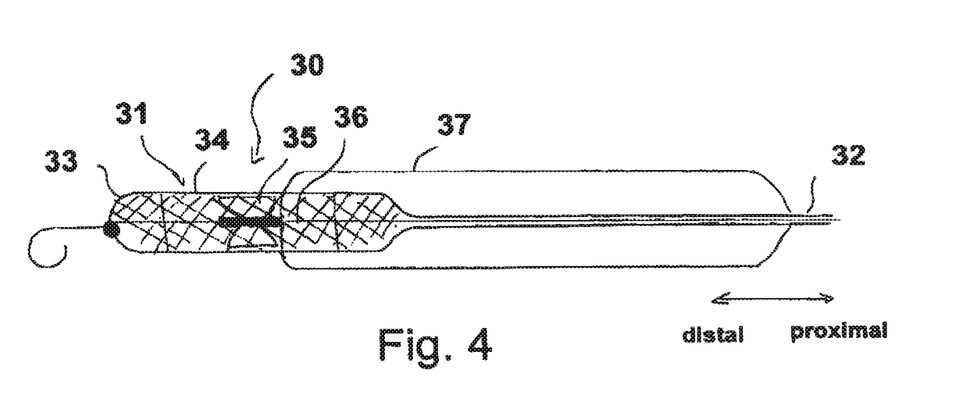
FIG. 4 an embodiment of a pump.
Figure 5:
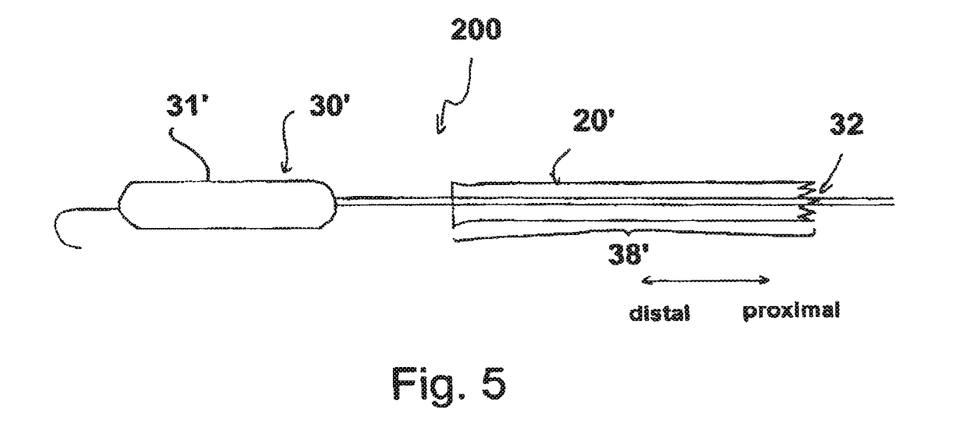
FIG. 5 an embodiment of a system according to the second aspect of the invention.
Figure 6:
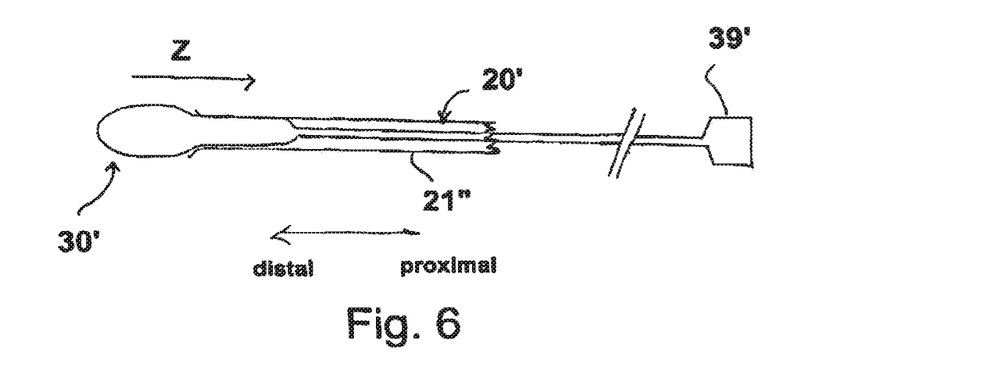
FIGS. 6, 7 pulling a pump into a second sheath.

Advantageous developments of this catheter pump (see previous paragraph) can be detected from the originally filed FIGS. 1 to 15b, in particular from FIG. 4, 5 or 6.

All the embodiments or originally filed patent claims mentioned here, provided that this is not technically contradictory, should be valid as possible developments.

The basic principle mentioned in the originally filed patent claim 23 is based on the fact (this applying of course to all aspects of the application) that the introducer sheath itself does not compress the rotor but that this takes place directly by means of a housing surrounding the rotor. In other words, a fixed spatial arrangement exists between the rotor and the housing surrounding the rotor, i.e. the rotor is not moved independently of the surrounding housing. The fixed spatial arrangement may be understood as the proximal or distal end of the rotor being feed with respect to at least one location of the surrounding housing. This housing can (as shown in this application) have a grid structure which is closed in regions. As a result, suction of fluid into the housing is possible and conveyance to the proximal end of the catheter is possible. The mentioned rotor can have various forms, for example it can have different rotor blades, these individual rotor blades being also able to have lamellae. The rotor can also have an outer plastic material surface and be configured for example as a plastic material cast or injection moulded part. It is important that the rotor can also have a compressed state for introduction into the vessel (or the housing/the sheath) and also an expanded state in which a conveying operation is possible and in which the rotor is protected by the surrounding housing. A gap between the radial rotor outer edges and the housing can hereby exist.

Even during operation the housing can he disposed still in regions in the introducer sheath close to the rotor as long as free rotation of the rotor is not impeded as a result.

Furthermore, the shaft can be coupled to the motor by means of a magnetic coupling.

The above-mentioned inventions are therefore suitable in particular for self-decompressible pumps.

BRIEF DESCRIPTION OF THE DRAWINGS

The invention is intended to be explained subsequently in more detail with reference to a few embodiments. There are shown.

DETAILED DESCRIPTION OF THE INVENTION

As already mentioned initially, FIG. 1 shows a schematic representation of a human vascular system in which a first sheath 10 configured as an introducer sheath has been introduced into the femoral artery with application of the Seldinger technique.

In FIG. 1, a guide wire 12 which extends into to the left ventricle is shown furthermore. The tubular portion 11 of the first sheath 10 is introduced into the artery such that the proximal end of the first sheath 10 is situated outside the femoral artery and hence can be used to introduce for example a pump. On the one hand, it is possible to thread the pump onto the guide wire 12 in order to guide the pump into the left heart ventricle by means of the guide wire.

It is a method according to the invention to guide the tubular portion 11 of the first sheath 10, guided by the guide wire, into the left ventricle and subsequently to remove the guide wire 12 from the first sheath. A possible pump unit is subsequently guided through the first sheath lumen into the vicinity of or into the left ventricle 4.

The invention is presently represented merely with reference to introduction of a pump into the left ventricle for assisting a heart function. However, it can be detected easily toy the person skilled in the art that the pump can be disposed also at other positions in the natural body vascular system. Furthermore, it is evident to the person skilled in the art that the invention is not restricted exclusively to the natural body vascular system but is suitable for introduction of a pump into any lumina. This includes for example lumina which are defined by tubes, into which a pump unit is intended to be introduced for conveying a flow.

Figure 2:
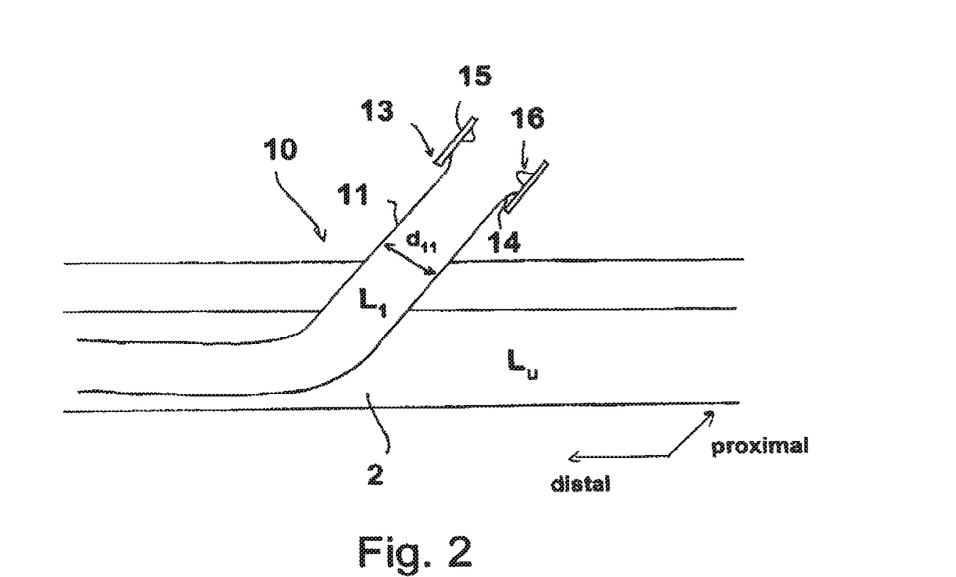
FIG. 2 a detailed view of a cut-out of FIG. 1.

In FIG. 2, the region of FIG. 1 in which the first sheath 10 is guided through the natural body tissue from outside into the lumen $L_G$ of the femoral artery 2 is represented. The first sheath thereby comprises a tubular portion 11 which is connected proximally to a valve 13. The tubular portion 11 defines a lumen $L_1$ which has an inner diameter $d_{11}$. The latter widens in the manner of a trumpet towards the proximal end of the tubular portion 11. The trumpet-like widening 14 leads to the diameter of the valve 13 being greater than the inner diameter $d_{11}$.

The valve 13 concerns a haemostatic valve which is known in prior art and comprises a housing 15 and a gasket 16. The haemostatic valve prevents fluid situated in the lumen $L_G$ from emerging outwards through the lumen $L_1$.

Figure 3:
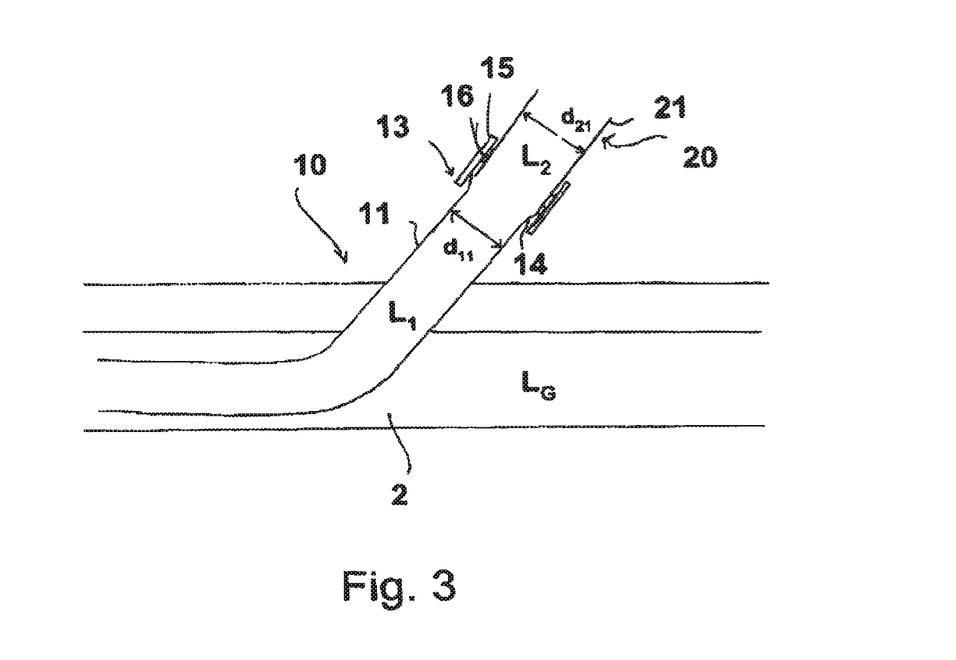
FIG. 3 an embodiment of a system according to the first aspect of the invention.

In the illustration of FIG. 3, the first sheath 10 of FIG. 2 is coupled to a second sheath 20. Merely a tubular portion 21 of the second sheath 20 which defines a lumen $L_2$ with an inner diameter $d_{21}$ is shown. The distal end of the second sheath 20 which is coupled to the valve 13 thereby has such an outer diameter that it can be introduced into the valve 13. The inner diameter $d_{21}$ is however greater than the inner diameter $d_{11}$.

At this point, reference may be made to the fact that the position of the valve is not restricted to the proximal end of the first sheath but can also be disposed at other positions inside the first sheath, such as for example the distal end of the first sheath or in the centre. It is sufficient for introducing the distal end of the second sheath into the proximal end of the first sheath if the proximal end of the first sheath has an inner diameter which is greater than the outer diameter of the distal end of the second sheath. The diameter of the lumen of the first and second sheath (apart from the proximal end of the first sheath and the distal end of the second sheath) can be uniform or different or the lumen of the respective sheath can be tapered.

The first and second sheath and also the distal pump unit are configured such that the distal pump unit can come to be situated in the first and second sheath, whilst the proximal end of the second sheath is situated in the distal end of the first sheath or is coupled thereto.

A pump situated in the lumen $L_2$, not illustrated, tan now be transferred from the second sheath lumen $L_2$ into the first sheath lumen $L_1$ by pressing. Subsequently, the pump is transported through the first sheath lumen $L_1$ to the position in the vascular system at which the pump is intended to develop its action. The pump can either be guided on a guide wire or be introduced without a guide wire through the first sheath lumen.

A possible embodiment of a pump 30 is explained in more detail with reference to FIG. 4. The pump 30 comprises a distal pump unit 31 and a shaft catheter 32 which abuts against the proximal end of the distal pump unit 31. At its proximal end, not illustrated, the shaft catheter 32 has a coupling for coupling the shaft catheter 32 to a drive device. The drive device sets a flexible shaft which extends in the shaft catheter 32 in rotation, which shaft in turn actuates the distal pump unit 31.

The distal pump unit comprises a pump housing 33 which is produced from intersecting nitinol struts. The nitinol housing is provided in parts with a coating 34 which extends distally and proximally to a rotor 35 disposed in the housing 33. The rotor is connected to the shaft 36 which extends through the shaft catheter 32 and is thus set in rotation. The housing and the rotor are compressible, i.e. the pump is s self-compressible pump. The unfolding of the pump is performed after the distal pump unit is pushed out of the distal end of one sheath. For compression of the pump, the distal pump unit is pulled into the distal end of a sheath lumen. The sheath lumen thereby has an inner diameter which is at least greater than the outer diameter of the shaft catheter.

The distal pump unit is constructed such that the housing surrounding the pump is essentially fixed in the axial direction relative to the rotor, i.e. the rotor is not removed from the housing during the implantation but remains in the same.

Optionally, the pump has a discharge hose 37 which defines a flow channel for the pumped fluid, situated proximally to the rotor 35. At the proximal end of the discharge hose 37, outlet openings which are not illustrated in more detail are situated.

Of course, the pump can also be switched from a pumping operation to a suction operation so that the pump no longer conducts fluid from the distal end to the proximal end, but vice versa.

A detailed description of a further suitable pump can be deduced for example from the publication EP 2 047 872 A1.

The function of the system according to the second aspect is now intended to be explained with reference to FIGS. 5 to 9.

In FIG. 5, a pump 30' which corresponds essentially to the pump 30 according to FIG. 4 is represented. For simplification, details of the pump are not shown. Merely the bulbous housing and also the "pigtail" situated distally to the bulbous housing are represented, which housing prevents suction of the heart pump against the heart wall. The shaft catheter 32' extends proximally to the distal pump unit 31'. Surrounding a region 38' of the shaft catheter 32', a second sheath 20' is disposed, which comprises a lumen $L_2$, the inner diameter $d_{21}$ of which is less than the diameter of the distal pump unit 31' in the decompressed or unfolded state.

The pump 30' illustrated in FIG. 5 is a compressible pump, i.e. the distal pump unit 31' which comprises infer alia the pump housing and the rotor situated therein is configured such that it can be compressed, i.e. reduced in its diameter. After a quality tester or for example a doctor has been able to convince himself of the correct function of the pump 30', e.g. by observing the rotational movement of the rotor unit situated in the distal pump unit 31' during a test run, the distal pump unit 31' is pulled into the lumen $L_2$ of the second sheath 20' by pulling the shaft catheter 32' in the proximal direction. By pulling the pump into the second sheath 20', bending or damage to the shaft catheter or the shaft extending therein is avoided. The pump 30' illustrated in FIG. 5 and the second sheath 20' surrounding the region 38' of the shaft catheter 32' form a system 200 which makes it possible to test the function of the pump 30' well before an operation and subsequently to compress the pump by pulling the distal pump unit 31' into the distal end of the second sheath 20' and thereby to avoid damage to the shaft.

Although the system according to the first and second aspect can be produced both with actively decompressible pumps and with self-decompressible pumps, it is suitable in particular for self-decompressible pumps, i.e. pumps, the distal pump unit of which outside the sheath automatically assumes the original size again.

In FIG. 6, an intermediate step when pulling the distal pump unit 31' into the lumen $L_2$ of the second sheath 20' is represented. It is detectable that the distal pump 31' is compressible and can be brought to a smaller diameter, so that the distal pump unit 31' can be received in the lumen $L_2$ of the second sheath 20'.

Furthermore, a coupling 39' which abuts against the shaft catheter 32' is represented in FIG. 6, which coupling enables coupling of the shaft extending in the shaft catheter to a drive unit. Since the coupling 39' has an often larger outer diameter than the inner diameter of the lumen $L_2$, the second sheath 20' is generally put on in the distal direction before assembly of the coupling 39' from the proximal end of the shaft catheter 32' so that the pump in system 200, i.e. the pump with the second sheath 20' situated proximally to the distal pump unit 31' and the premounted coupling 39', is delivered. In FIG. 6, a slight trumpet-like widening of the distal end of the second sheath 20' is represented. The trumpet-like widening 24' facilitates pulling the distal pump unit 31' into the lumen $L_2$ of the second sheath 20'.

Figure 7:
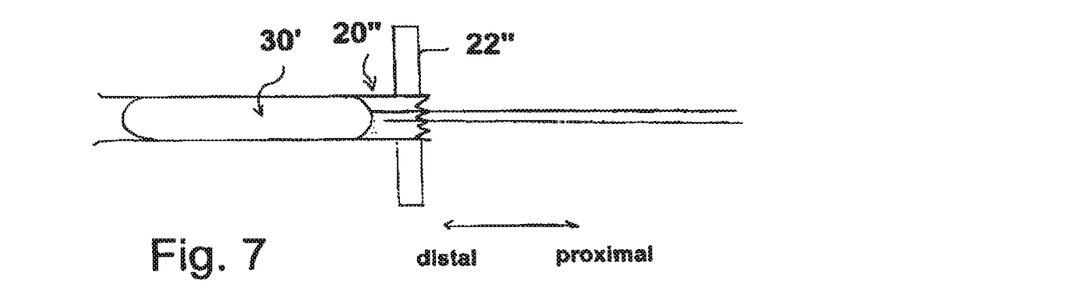

In FIG. 7, the distal pump unit 31' is finally situated completely in the lumen $L_2$ of the second sheath 20". The second sheath 20" differs from the sheath 20' merely by two premounted gripping units 22" which enable better holding or removal of the second sheath 20" when pulling the distal pump unit 31' into the lumen $L_2$ or subsequent tearing off. Advantageously, in the case of a "pigtail" being present, this is likewise pulled into the lumen $L_2$ so that the distal pump unit 31' together with components of the pump situated distally to the distal pump unit 31' is situated in the lumen $L_2$.

Figure 8:
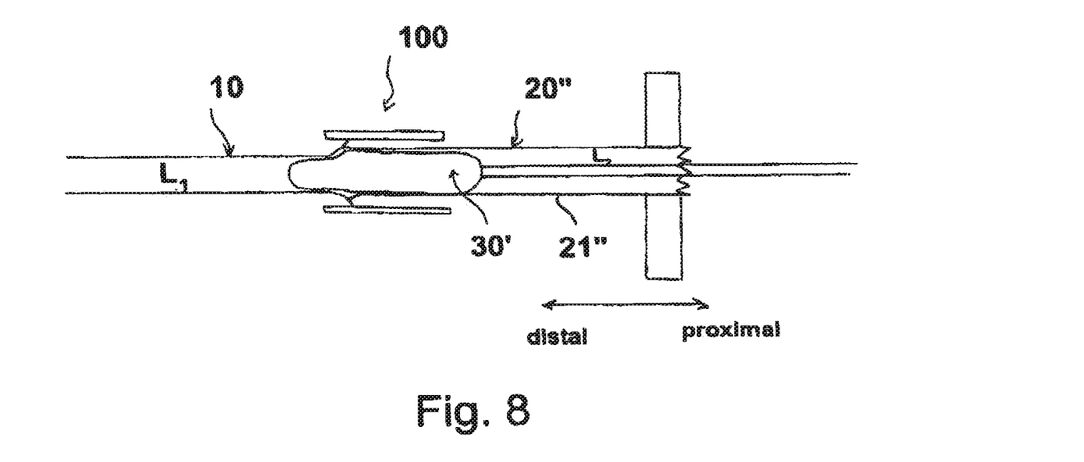
FIG. 8, 9 transfer of a pump from a second into a first sheath.

In FIG. 8, it can be detected how the system 200 comprising pump 30' and second sheath 20" is combined in operating connection with the first sheath 10 to form a system 100 according to the first aspect of the invention. Firstly, the second sheath 20" is introduced by its distal end into the valve of the first sheath 10. As soon as the distal tip of the second sheath 20" abuts against the trumpet-like widening 14 of the first sheath 10, by pushing the pump in the distal direction, the pushing being effected by means of pushing the shaft catheter 32', the pump is transferred, from the second sheath 20' into the first sheath 10'. The diameter of the distal pump unit 31' is hereby reduced further to the inner diameter $d_{11}$ of the lumen $L_1$.

Figure 9:
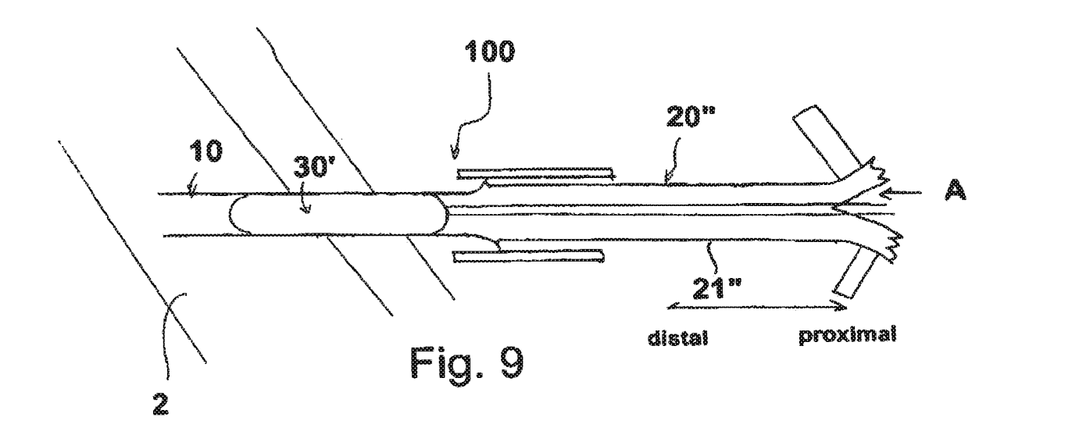

In FIG. 9, the subsequent step in which the distal pump unit 31' is situated completely in the lumen $L_1$ of the first sheath 10 is represented. The fact that the distal pump unit 31' is situated completely in the lumen $L_1$ of the first sheath 10, can be identified for example with reference to a colour marking 50 which is applied on the outside of the shaft catheter 32'.

Subsequently, the second sheath 20", which is configured as a "peel-away" sheath, is removed from the shaft catheter 32' by tearing off the peel-away sheath from the proximal towards the distal end and pulling it off the shaft catheter 32'. The directed tearing off from the proximal to the distal end can be assisted by notches A but is based predominantly on the orientation of the molecular chains of the plastic material which is used from the proximal to the distal direction.

After the peel-away sheath has been removed, the pump 30' is guided again inside the lumen $L_1$ of the first sheath 10 up to the desired position.

Reinforcement of the second sheath 20" is unnecessary, in particular when pulling the distal pump unit 31' into the distal end of the second sheath lumen $L_2$ since the danger of bending of the shaft during a pulling movement is greatly reduced.

During transfer of the pump from the second sheath into the first sheath, as illustrated with reference to FIGS. 7 to 9, the second sheath can include a structure which reinforces it in the form of an introduced wire, or the tubular portion 21" of the sheath 20" is not produced from a flexible plastic material but from a fixed-shape plastic material or metal.

A further possibility for pulling the pump into the second sheath, when moving forwards in the pump 30' in the distal direction, i.e. in particular when transferring the pump 30' from the second sheath into the first sheath, resides in retaining the second sheath 20" by means of a device 40 for retaining the second sheath.

Figure 11:
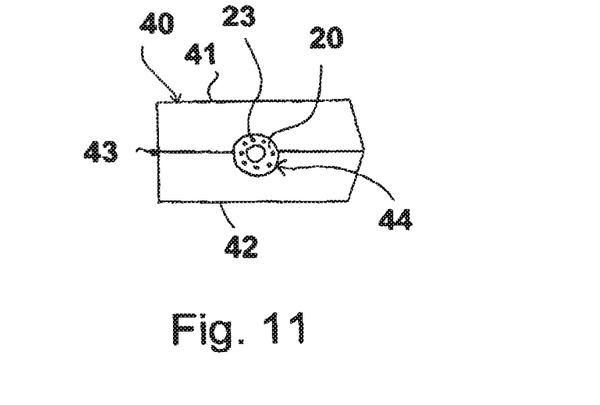
FIG. 11 a cross-section of the representation of FIG. 10.

The device for retaining a portion of the second sheath 20" is represented in cross-section in FIG. 11. The device 40 has an upper and a lower half 41 or 42 which are connected to each other via a hinge 43. In the first or second half 41 or 42 there is situated respectively a recess, the recesses in the illustrated, closed state of the device 40 defining a cavity 44. The cavity 44 configured as a lumen is configured furthermore such that a second sheath 20 can be retained frictionally in the cavity. This can be achieved either via correspondingly chosen inner diameters of the cavity 44 or outer diameters of the second sheath 20 or rough surfaces in the region of the cavity 44. Also knobs in the region of the cavity 44 can produce a frictional fit.

Figure 10:
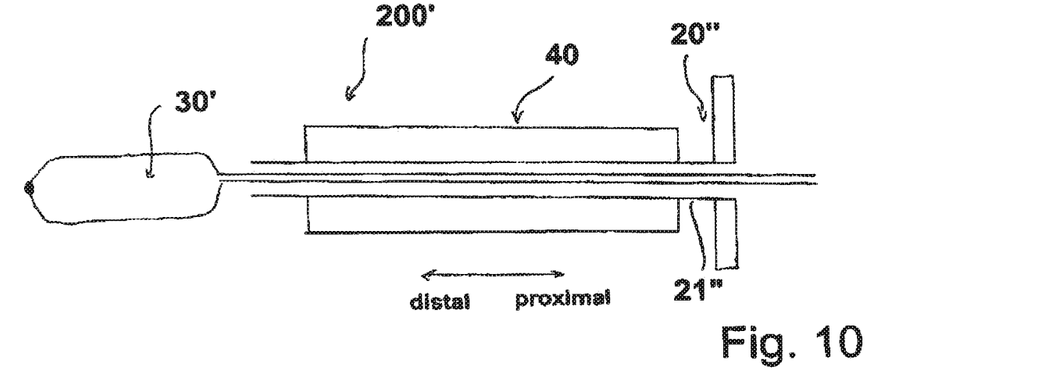
FIG. 10 an embodiment of the system according to the second aspect with a device according to the third aspect of the invention.

As can be detected with reference to FIG. 10, the cavity 44 extends without, curvature and hence does not allow any bending of the shaft which extends in the shaft catheter 32' if the latter is pushed forwards in the distal direction by means of a transverse force. In addition, the device 40 makes an improved grip possible for an operator of the system 200' for introducing the pump.

Figure 12:
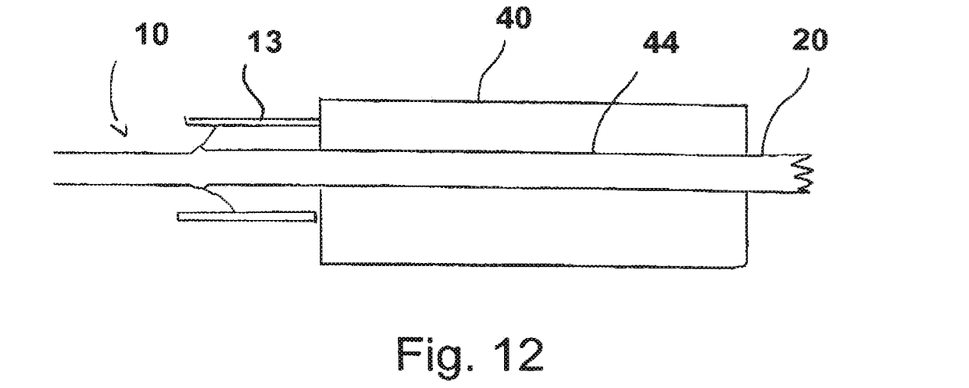
FIG. 12 an embodiment according to the first and third aspect of the invention.

In FIG. 12, the device 40 with the cavity 44 in which a second sheath 20 is retained is represented. The distal end of the device 40 thereby lies on the proximal end of the valve 13 of the first sheath 10. In the case of such a coupling between the first sheath 10 and the second sheath 20, simplified introduction of a pump from the second into the first sheath can be achieved.

Figure 13A:
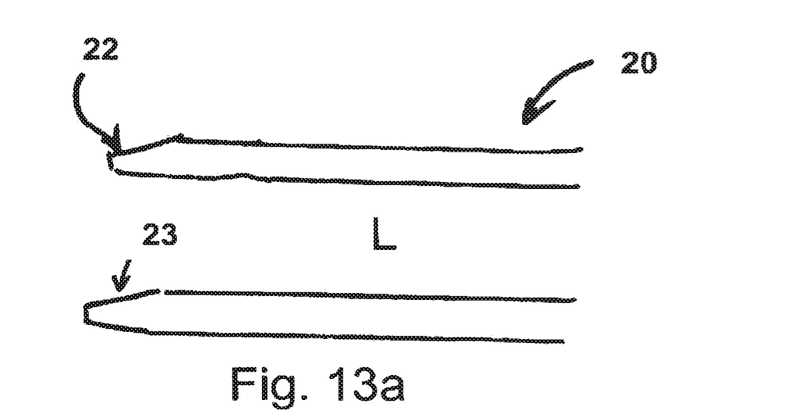
FIGS. 13a and 13b an embodiment of a distal end of a sheath according to the second aspect of the invention.

In FIG. 13a, a distal end 22 of an embodiment of the sheath 20, according to the second aspect of the invention is represented. The distal end 22 has an internal and external tapering of the edge 23 surrounding the lumen L, as a result of which an improved introduction of the sheath into the natural body lumen or a first sheath according to the first aspect of the invention is possible. Likewise, the distal end 22 can be the end of second sheath according to the first aspect of the invention. A possible proximal end can have the same shape of configuration.

Figure 13B:
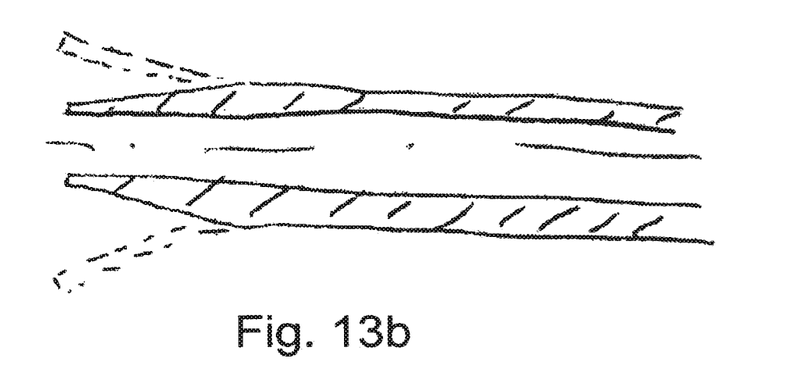

FIG. 13b shows a further variant; an additional feature hereby is that the distal end has such a flexible or elastic configuration that it widens slightly when pulling in the pump head and consequently facilitates insertion. After complete insertion of the pump head, the distal end again adopts extensively the original shape. During introduction of the distal end of the second sheath into the first sheath, the distal end of the second sheath can also be fitted by the elastic/flexible tapering to the proximal end of the first sheath and consequently can facilitate coupling.

The systems, represented in the present documents, according to the first, second and third aspect hence enable simplified handling and improved introduction of pumps into a lumen.

Subsequently, another possible variant of a method for introducing a pump into a left ventricle is intended to be portrayed. As a preparatory measure, the pump is firstly filled with sterile physiological common salt solution and hence completely deaired. Subsequently, the peel-away sheath placed proximally to the distal pump unit is pushed forwards up to a possibly present discharge hose. The peel-away sheath has a diameter of approx. 10 Fr. After the peel-way sheath has been pushed forwards up to the discharge hose, the peel-away sheath is surrounded by the device for retaining the second sheath. Subsequently, the distal pump unit, possibly with a slight rotational movement is pulled into the peel-away sheath by exerting a pulling movement on the shaft catheter in the proximal direction. The pump is displaced into the second sheath until a possibly present pigtail is likewise hidden in the peel-away sheath. By means of these steps, it is possible to test the functional capability of the pump even before an operational procedure and to introduce the pump only subsequently into a sheath without requiring to act under pressure of time. For example, the puncturing of the vascular system for introducing the first sheath is only implemented subsequently. In order to save time, it is however also possible in this way that an assistant prepares the pump whilst the user already implements the puncturing in parallel.

After for example a 9 Fr introducer sheath has been introduced into the left ventricle, a possibly present dilator is pulled out of the introducer sheath and removed therefrom.

Subsequently, the pump retained in the peel-away sheath, which is surrounded for example by the device for retaining the second sheath, for example a 2 cm long portion of the distal end of the peel-away sheath protruding at the distal end of the device, is coupled to the haemostatic valve of the introducer sheath until the tip of the peel-away sheath abuts inside the introducer sheath. Subsequently, the pump is transferred from the peel-away sheath into the introducer sheath by pushing the shaft catheter.

As soon as the distal pump unit has been transferred completely into the introducer sheath, as can be checked for example with reference to an optical marking on the shaft catheter shaft, the device for retaining the second sheath can be removed from the second sheath and the peel-away sheath can be torn off and withdrawn from the shaft catheter. Subsequently, the pump is pushed forwards inside the introducer sheath up to the left ventricle. The introducer sheath is subsequently pulled back from the left ventricle tip to the beginning of the descending aorta.

The positioning of the distal pump unit in the left ventricle can be Checked for example by radioscopy. For this purpose, an X-ray-visible marking is situated on the pump housing or the pump housing itself is X-ray-visible. Likewise, the outlet region, i.e. the outflow openings of a discharge hose, should be situated in the region of the ascending aorta. This can also be checked with an X-ray-visible marking. A possibly present pigtail catheter tip should abut against the tip of the left ventricle.

In order to remove the pump from the ventricle, this is pulled back into the introducer sheath by means of a tensile force applied on the shaft catheter and is removed, in a compressed state, from the arterial vascular system. Subsequently, the introducer sheath and further remaining components are removed from the vascular system.

A further aspect of the invention is the use of a long sheath during implantation and explantation of the pump. The long sheath serves not only, as is common in prior art, for introducing the pump into a natural body lumen but for guiding the pump through the sheath lumen to the vicinity of the operating location. It is hereby advantageous if, in the medical field, the sheath has a length between 40 and 120 cm. The length is generally determined by the subsequent operating location of the pump and the physical constitution of the patient. The long sheath can be provided, on the one hand, by the first sheath of the system according to the first aspect of the invention and, on the other hand, by the sheath of a system according to the second aspect of the invention.

A schematic representation of a long sheath and of the distal pump unit in the operating state cars be deduced from FIG. 14.

The long sheath 60, which is formed by a first or second sheath of the system according to the first aspect of the invention or a sheath of the system according to the second aspect of the invention, ends at the aortic arch 3, the shaft catheter 32 of the pump 30 extending through the lumen of the long sheath and emerging at the distal end of the sheath lumen. The distal pump unit 31 is located in the ventricle 4 in the operating state.

Alternatively, the length of the long sheath can be chosen such that this ends in the ventricle before decompression of the pump so that the distal pump unit is unfolded only in the ventricle.

At the proximal end of the long sheath, the coupling 39' is situated, which serves for coupling the shaft which extends in the shaft catheter to a drive unit.

The long sheath has such a length that it is possible to place the distal pump unit in the vicinity of the operating location.

Essentially two functions are attributed to the long sheath. One the one hand, the long sheath enables guidance of the pump to the operating location. Since the pump is compressed in the sheath lumen of the long sheath, conveyance of the pump to the place of use, relative to sole guidance by a guide wire, is simplified. In addition, this serves for avoiding complications or injury to the inner vascular walls. In particular in the case self-unfolding pumps, i.e. pumps which have no active actuatable components for unfolding the distal pump unit, this is a significant simplification relative to guidance of the pump unit by means of a guide wire. On the other hand, the long sheath enables simplified explantation of the pump. The pump unit, after completion of the conveying performance, is pulled into the distal end of the long sheath by a pulling movement of the shaft catheter, consequently compressed and subsequently withdrawn either through the sheath, lumen of the long sheath or pulled, together with the long sheath, out of the natural body lumen.

If the pump is withdrawn together with long sheath, out of the natural body lumen, bleeding of the femoral artery is stopped with a pressure bandage. Alternatively, the pump can be withdrawn from the sheath lumen of the long sheath. Then a further guide wire can be placed through the lumen of the sheath, via which then, after removal of the sheath, a device for closing the puncture can be guided. As a result, improved stoppage of the bleeding can be achieved.

If the first sheath of the system according to the first aspect of the invention is configured as a long sheath, a system according to the second aspect can be introduced into the proximal end of the long sheath. Subsequently, the second sheath is possibly withdrawn from the shaft catheter and the pump is guided through the sheath lumen of the long sheath to the operating location of the pump.

As an alternative hereto, the long sheath can also be formed by a sheath in the sense of the system of the second aspect of the invention. A first sheath, in the sense of the first aspect, can then be dispensed with. In this variant, the distal pump unit of the pump is firstly pulled into the distal end of the sheath lumen of the sheath according to the second aspect of the invention. Subsequently, the sheath in the sense of the second aspect is transferred for example with the help of the Seldinger technique into the natural body lumen. The sheath is then pushed into the vicinity of the operating location of the pump. The pushing is thereby effected preferably on the outside of the sheath. In order to be able to apply this method, the pump is guided via a guide wire. This can be guided for example by a guide wire lumen of the catheter tip or an additional lumen of the sheath.

Conveyance of the pump to the operating location is possible in different ways. After the sheath is situated with its distal end in a natural body lumen, the pump can be guided to the operating location by pushing the shaft catheter out of the sheath and outside the latter, it must hereby be ensured that the pump unit must be pushed in the unfolded state through the natural body vessel on the basis of the absence of compression force of the sheath lumen. In this variant, a long sheath is not required.

Although a possible alternative for guiding the pump unit to the operating location is present in the above-described variant, it is preferred to guide the pump in the folded or compressed state inside the sheath lumen to the vicinity of the operating location. For guidance of the sheath inside the vascular system, a rapid-exchange technique can be used, on the one hand, a guide wire being coupled for example to a possibly present catheter tip and the sheath being pushed along the guide wire. Alternatively, the sheath can include a further sheath lumen for receiving a guide wire, the sheath being pressed forwards towards the guide wire.

After the distal pump unit has been pushed out of the distal end of the sheath lumen, the pump is displaced forwards merely by a small distance. The small distance in the case of the human heart as operating location of the pump is less than 20 cm. In the ratio to the total length of the long sheath, a small distance is defined by a ratio of the total length to the small distance of 3:1 or more.

The sheath can remain for the period of treatment in the natural body vascular system—surrounding the shaft catheter. In this case, the pump can be pulled into tire distal end of the sheath for explantation and subsequently, as described in one of the preceding paragraphs, be removed from the natural body vascular system.

Alternatively, if the long sheath concerns a tear-off sheath, this can be withdrawn and removed after guiding the pump to the operating location. An explantation of the pump is then no longer possible by means of the sheath. An additional tool is required, which enables the explantation of the pump and forms an independently patentable subject of the invention.

The additional tool is only introduced into the vascular system at the time of the explantation. The additional tool has a lumen for introducing the distal pump unit. During introduction of the additional tool, it must be ensured that no non-sterile regions of the shaft catheter are crossed. By crossing non-sterile regions, germs can be introduced into the vascular system. In order to achieve a germ-free introduction of the additional tool, it is possible to pull a portion of the shaft catheter situated in the vascular system out of the lumen since the portion formerly situated in the vessel normally has no foreign germs. The non-sterile region of the shaft catheter which lies outside the patient during use of the pump and which extends up to the drive coupling is removed for example by cutting off. The shaft catheter can also have a suitable predetermined breaking point. In this case, the additional tool can have a tubular or hose-shaped configuration and can be guided directly via the severed catheter end. A possible handle would facilitate handling.

The lumen of the additional tool has an inner diameter which corresponds essentially to the outer diameter of the catheter to be explanted or to the outer diameter of the again compressed pump head. During separation of the non-sterile regions of the shaft catheter, it must hence be ensured that only components of the pump which can be inserted into such a created lumen remain distally to the distal end of the additional tool.

Alternatively, the additional tool can be configured in the form of a longitudinally divisible tube. In this case, separation of the non-sterile catheter region would be unnecessary since the tool can also be placed directly on the withdrawn region.

In the preceding examples, the system according to the second aspect of the invention was described such that, when the system is delivered, the sheath is situated proximally to the distal pump unit and the distal pump unit is pulled by the user of the pump into the distal end of the sheath lumen of the sheath. This has the advantage that the user can test the functional efficiency of the pump in advance. Alternatively, the system can also be delivered even already with an inserted distal pump unit. The test run of the pump then takes place at the workplace.

If the pump is a self-decompressible pump, the second sheath of the system, according to the first aspect of the invention, which serves inter alia for compression of the distal pump unit, can be replaced, in a variant of the system according to the first aspect of the invention, by a crimping tool.

The crimping tool has, at its distal end which is coupled to the proximal end of the first sheath, for example a diaphragm which effects compression of the distal pump unit of the pump when the distal pump unit is intended to be transferred into the first sheath. The diaphragm can be part of a funnel-shaped tapering, the diaphragm being situated at the distal end of the tapering.

If a crimping tool is used, the distal pump unit is transferred by pushing into the first sheath of the system according to the first aspect of the invention.

In summary, the systems according to the first, second and third aspect form independent inventions. Further variants of the invention are provided by a system according to the second aspect with a long sheath, a system according to the first aspect with a long first sheath, a system according to the first aspect with a long second sheath, a system according to the first aspect with a crimping tool, possibly instead of a second sheath. The corresponding embodiments of the system according to the first, second and third aspect can be applied likewise to the further variants of the invention.

The presented treatment methods are likewise included by the invention. This relates in particular to the implantation and/or explantatlon of the pump by means of a long sheath. Also the variants of the invention cited in the preceding paragraph are suitable for implantation and/or explantation, as described in the present application.

The invention claimed is:

1. An intracardiac blood pump system comprising:
a sheath for delivering an intracardiac blood pump assembly percutaneously, the sheath having a flared distal end with a continuous surface, the distal end formed of a fixed-shape material; and
the blood pump assembly coupled to the flared distal end of the sheath, the blood pump assembly comprising:
a proximal section with an outer diameter that is smaller than an inner diameter of the sheath,
a radial shoulder adjacent to and distal from the proximal section, wherein the radial shoulder has a constant outer diameter that is larger than an outer diameter of the flared distal end of the sheath, and
a distal portion with an outer diameter that is smaller than the outer diameter of the shoulder.

2. The system of claim 1, wherein the proximal section is positioned inside the flared distal end of the sheath such that the radial shoulder abuts the flared distal end of the sheath.

3. The system of claim 2, wherein movement of the blood pump assembly in a proximal direction relative to the sheath is limited by the radial shoulder abutting the flared distal end of the sheath.

4. The system of claim 3, wherein the flared distal end of the sheath is a trumpet-like widening which facilitates movement of the blood pump assembly into the sheath.

5. The system of claim 1, wherein the sheath is a tear-off sheath which can be torn off.

6. The system of claim 1, wherein the sheath is formed at least in part of plastic.

7. The system of claim 1, further comprising a drive shaft coupled to the blood pump assembly, and a rotatable impeller disposed on the drive shaft.

8. The system of claim 7, wherein the rotatable impeller in a compressed state can be introduced into a blood vessel within the sheath.

9. The system of claim 8, wherein the rotatable impeller can operate in an expanded state when the sheath is removed.

10. The system of claim 7, wherein the rotatable impeller can be compressed into the sheath for withdrawal from a blood vessel.

11. The system of claim 1, wherein the fixed-shape material is not flexible.

12. The system of claim 1, wherein the fixed-shape material is metal.

13. An intracardiac blood pump system comprising:
a sheath for delivering an intracardiac blood pump assembly percutaneously, the sheath having a flared distal end with a continuous surface; and
the blood pump assembly configured to slide in proximal and distal directions relative to the flared distal end of the sheath, the blood pump assembly comprising:
a proximal section with an outer diameter that is smaller than an inner diameter of the sheath, and
a radial shoulder adjacent to and distal from the proximal section, wherein the radial shoulder has a constant outer diameter that is larger than an outer diameter of the flared distal end of the sheath,
wherein the flared distal end of the sheath has a fixed shape.

14. The system of claim 13, wherein the proximal section is configured to be positioned inside the flared distal end of the sheath such that the radial shoulder abuts the flared distal end of the sheath.

15. The system of claim 14, wherein movement of the blood pump assembly in the proximal direction relative to the sheath is limited by the radial shoulder abutting the flared distal end of the sheath.

16. The system of claim 15, wherein the flared distal end of the sheath is a conical widening which facilitates movement of the blood pump assembly in the proximal direction into the sheath.

17. The system of claim 13, wherein the sheath is a tear-off sheath which can be torn off.

18. The system of claim 13, further comprising a drive shaft coupled to the blood pump assembly, and a rotatable impeller disposed on the drive shaft.

19. The system of claim 18, wherein the rotatable impeller in a compressed state can be introduced into a blood vessel within the sheath.

20. The system of claim 19, wherein the rotatable impeller can operate in an expanded state when the sheath is removed.

21. The system of claim 18, wherein the rotatable impeller can be compressed into the sheath for withdrawal from a blood vessel.

* * * * *

UNITED STATES PATENT AND TRADEMARK OFFICE
CERTIFICATE OF CORRECTION

PATENT NO. : 10,874,781 B2
APPLICATION NO. : 14/985217
DATED : December 29, 2020
INVENTOR(S) : Thomas Toellner It is certified that error appears in the above-identified patent and that said Letters Patent is hereby corrected as shown below:

In the Specification

Column 1, Line 6:
Now reads: "PCT/EP2011/003 187,"; should read -- PCT/EP2011/003187, --

Column 2, Line 3:
Now reads: "giving"; should read -- driving --

Column 3, Line 35:
Now reads: "rumen"; should read -- lumen --

Column 3, Line 49:
Now reads: "puffing"; should read -- pulling --

Column 4, Line 21:
Now reads: "pomp"; should read -- pump --

Column 4, Line 28:
Now reads: "embodiment,"; should read -- embodiment --

Column 4, Line 39:
Now reads: "he"; should read -- be --

Column 4, Line 46:
Now reads: "horn"; should read -- from --

Column 6, Line 14:
Now reads: "primp"; should read -- pump --

Signed and Sealed this
First Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,874,781 B2

Column 6, Line 23:
Now reads: "far"; should read -- for --

Column 6, Line 52:
Now reads: "feed"; should read -- fixed --

Column 7, Line 1:
Now reads: "he"; should read -- be --

Column 7, Line 23:
Now reads: "FIG."; should read -- FIGS. --

Column 7, Line 62:
Now reads: "toy"; should read -- by --

Column 8, Line 43:
Now reads: "tan"; should read -- can --

Column 8, Line 66:
Now reads: "s"; should read -- a --

Column 8, Line 67:
Now reads: "self-compressible"; should read -- self-decompressible --

Column 9, Line 38:
Now reads: "infer"; should read -- inter --

Column 10, Line 25:
Now reads: "31'is"; should read -- 31' is --

Column 10, Line 35:
Now reads: "transferred,"; should read -- transferred --

Column 11, Line 21:
Now reads: "without,"; should read -- without --

Column 12, Line 38:
Now reads: "tip"; should read -- up --

Column 12, Line 41:
Now reads: "Checked"; should read -- checked --

Column 13, Line 2:
Now reads: "cars"; should read -- can --

CERTIFICATE OF CORRECTION (continued)
U.S. Pat. No. 10,874,781 B2

Column 14, Line 8:
Now reads: "latter, it"; should read -- latter. It --

Column 14, Line 34:
Now reads: "tire"; should read -- the --

Column 14, Line 42:
Now reads: "required,"; should read -- required --

Column 15, Line 47:
Now reads: "explantatlon"; should read -- explantation --